Figure 1:
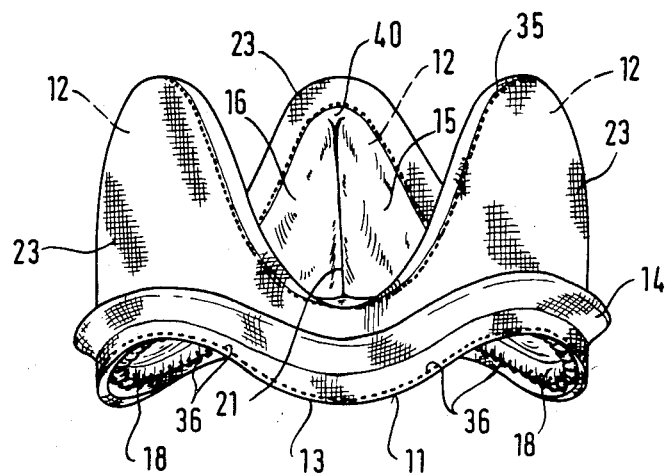

United States Patent [19]

Reichart et al.

[11] Patent Number: 4,626,255
[45] Date of Patent: Dec. 2, 1986

[54] HEART VALVE BIOPROTHESIS

[75] Inventors: Bruno Reichart, München, Fed. Rep. of Germany; Christian Weinhold, Hatzfelderweg 13b, 8000 München 71, Fed. Rep. of Germany

[73] Assignee: Christian Weinhold, Fed. Rep. of Germany

[21] Appl. No.: 652,774

[22] Filed: Sep. 19, 1984

[30] Foreign Application Priority Data

Sep. 23, 1983 [DE] Fed. Rep. of Germany ....... 3334512

[51] Int. Cl.$^4$ .............................................. A61F 2/24
[52] U.S. Cl. ....................................... 623/2; 623/900
[58] Field of Search ................................. 3/1.5, 1, 1.4

[56] References Cited

U.S. PATENT DOCUMENTS

| Re. 30,912 | 4/1982 | Hancock | 3/1.5 |
| 3,983,581 | 10/1976 | Angell et al. | 3/1.5 |
| 4,084,268 | 4/1978 | Ionescu et al. | 3/1.5 |
| 4,466,139 | 8/1984 | Ketharananathan | 3/1.4 |

FOREIGN PATENT DOCUMENTS

| 2451189 | 11/1980 | France | 3/1.5 |
| 8100009 | 9/1982 | Romania | 3/1.5 |

OTHER PUBLICATIONS

"Experimental Studies of the Anatomical and Functional Characteristics of Kangaroo Aortic Valve Bioprostheses", Life Support Systems, 1984, 2,121-126, Weinhold et al.
Implants: Reconstructing the Human Body, Lynch, 1982, p. 63.

Primary Examiner—Richard J. Apley
Assistant Examiner—James Prizant
Attorney, Agent, or Firm—Townsend and Townsend

[57] ABSTRACT

A heart valve prosthesis has a supporting frame (22) with a circular cross-section, which is covered with a dacron fabric (23). On one end face the dacron fabric (23) is arranged to form a suture ring (14). The fixed aortic valve (15,16,17) of a kangaroo is attached inside the frame and sutured to the dacron fabric (23).

11 Claims, 5 Drawing Figures

HEART VALVE BIOPROTHESIS

The invention concerns a heart valve bioprosthesis with a fixed, integral aortic valve of animal origin which is positioned in an resiliently flexible, fabric-covered supporting frame having substantially the shape of a cylinder with a substantially circular cross-section. The cylinder consists of an axially slightly undulatory annulus comprising three complete waves and of three rounded posts which are positioned at equidistant angles, and extend axially from the wave apices. These furthermore have number of perforations, the fabric being shaped as a suture ring near the end face opposite to the posts and the annulus, fibrosus from which the three aortic leaflets orrginate. In the area of which muscular tissue of the ventricular septum is to be found, extending along the end face of the supporting frame opposite to the posts and being sutured there to the fabric, and the aortic wall or stump, which is cut according to the shape of the supporting frame, being mounted within the annulus and said posts and being sutured to the fabric along the end face of the supporting frame on the side of the posts.

The implantation of heart valve bioprosthesis with biological tissue valves has become an acknowledged method all over the world due to the favourable results regarding postoperative morbidity, thrombo-embolism and general quality of life. Experience with porcine hearts goes back to 1970. The briefer lifespan of these prostheses compared to mechanical valves, premature calcification in young patients and higher transvalvular pressure gradients arising in the smaller valve sizes often lead to complications and the necessity for reoperation.

The latter is due to the rigid root of the right aortic leaflet which rests several millimeters on the muscular ventricular septum of the porcine heart. After removal and preparation of the valve the adhering remnants of muscular tissue become inelastic due to the process of fixation with glutaraldehyde, whereby the mobility of the right leaflet is impaired.

New methods have been developed in an attempt to solve this problem (reduction of the supporting cylinder height, modified fixing agents, low pressure fixation) and have lead to a modification of porcine bioprostheses.

These modifications entail a considerable increase in technical and manufacturing expenditure involved in the production of artificial valves and result in rising costs.

The invention is based on the recognition of the fact that in previously used porcine xenografts the basis of the right leaflet—seen from its attachment to the annulus fibrosus—coalesces for several millimeters with the muscular bulge of the ventricular septum. In order to eliminate this difficulty an attempt was made to remove any muscular tissue impairing the mobility of the right leaflet by preparation of the right leaflet starting from the annulus fibrosus. This was accomplished by mechanical means, i.e. scraping. Apart from expensive production procedures it is impossible to completely remove the impeding muscular tissue, so that during the following fixation process with 2% glutaraldehyde solution the remaining muscular fibres become rigid, thus impeding the mobility of the right leaflet near its root.

This is the reason why a heart prosthesis of this kind does not open wide enough during the opening cycle, thus leading to an undesirably high hemodynamic pressure gradient.

Attempts have been made to use larger porcine aortic valves in order to have enough material to be able to take the tissue of the right leaflet being coalesced with the muscular tissue out of the aortic lumen and to place it around the lower end face of the supporting frame. With this type of artificial valve the tissue of the right leaflet is pulled outwards over the frame whereby long term strain often leads to tears in the tissue with blood inflow and subsequent calcification of the sensitive line of fold.

Finally attempts have been made to assemble heart valve prostheses from individual leaflets. However apart from the considerable manufacturing expenditures involved, shorter endurance is to be expected as the numerous sutures have a weakening effect.

The object of the invention is to provide a heart valve bioprosthesis of the type mentioned above, in which the mobility, particularly of the right leaflet should resemble the mobility of a human valve as closely as possible whilst retaining the origination of the leaflet from an annulus fibrosus sutured to the lower rim of the fabric and without individual leaflets having to be assembled from different aortic valves.

The invention solves this problem by using an animal aortic valve in which the right leaflet as well as the other two leaflets protrude almost completely unobstructed from the annulus fibrosus into the aortic lumen, without being coalesced with muscular tissue of the ventricular septum.

A preferred embodiment of the invention is characterized in that the aortic valve has the shape, size and structure of a fixed aortic valve of an adult kangaroo, i.e. the aortic valve is preferably the fixed aortic valve of an adult kangaroo.

The invention is based on the recognition of the fact that it is important for an aortic valve, deadened by means of the process of fixation, to originate from the annulus fibrosus being attached to the dacron fabric in the area of the lower rim of the supporting frame, while not being coalesced at all with the muscular tissue of the ventricular septum, or only to such a minimal degree that mobility is hardly impaired. This requirement is ideally met by the aortic valve of a preferably male red or grey giant kangaroo of the species Macropus giganteus or Macropus rufus.

The production of the aortic valves involves the removal of the aortic root along with the adjoining myocardium and an aortic stump of several centimeters from a prefixed heart.

The advantage of the use of fixed aortic valves of the kangaroo lies particularly in the fact that the aortic wall extends along the sinus valsalvae with its elastic fibres and the smooth muscles up to the protruding muscular torus. Only then a very small, flat annulus fibrosus originates from this point, and is anchored to the muscular tissue of the septum by small individual collagenous fibre fingers. The right leaflet does not rest on the muscular torus, and does originate almost completely unimpeded from the annulus fibrosus into the aortic lumen.

Thus the invention comprises a heart valve prosthesis in which the origin of the right leaflet together with the much smaller annulus fibrosus is much shorter in relation, to the total diameter of the aortic ostium, than is the case with porcine xenografts. Thereby the portion of the right leaflet which is immobile after the process of fixing is reduced, which results in a significantly wider valvular lumen during the opening cycle compared to porcine xenografts. When the valves according to the present invention are used as xenografts less significant pressure changes occur than in the case of porcine valves.

Thus a considerable improvement in function is to be obtained, especially with smaller valve sizes. Aortic valves of the kangaroos can be produced in sizes between 17 mm and 31 mm. They can be used as replacement valves in any of the four positions of the heart, e.g. they can be employed as aortic or as mitral valves.

The supporting frame consists preferably of a thermally very stable plastic, for example an acetylcopolymer resin (Delrin). The fabric covering the frame is usually a double-knitted polyester product.

In order to make optimum use of the advantages of a fixed kangaroo aortic valve and particularly of the favourable opening ratio, the frame is shaped according to one of the forns disclosed herein.

The width of the posts intended for the arrangement of the commissures is according to invention about ¼ of the outer diameter of the carrier frame; furthermore according to invention the equidistant commissure posts are broad enough so as to allow a tolerance of 30° in the arrangement of the commissures. In comparison, kangaroo aortic valves show a variation in the arrangement of commissures of approximately 15°.

In accordance to invention as well, is the fact that the supporting frame exhibits considerably shorter commissure posts compared to supporting frames used for porcine valves to date. The total profile is also lower in the axial direction.

Another important characteristic of the invention is that the entrance edge facing away from the posts has an undulation gentle enough to not only allow a flat mitral suture ring to be fitted on, but also a curved aortic suture ring. The prosthesis can be especially advantageously integrated according to invention within a vascular prosthesis with a built in cardiac valve.

Also of special importance are the supporting frame's numerous holes, slots, oblong perforations, borings, which have been provided in every part of the frame and which not only serve to improve the elasticity of the frame considerably, but also offer plenty of possibilities for attachment of the tube-shaped dacron fabric which covers the frame from all sides. The width of the annular area has been chosen in such a way that a maximum of space for free mobility of the leaflets is available.

Figure 2:
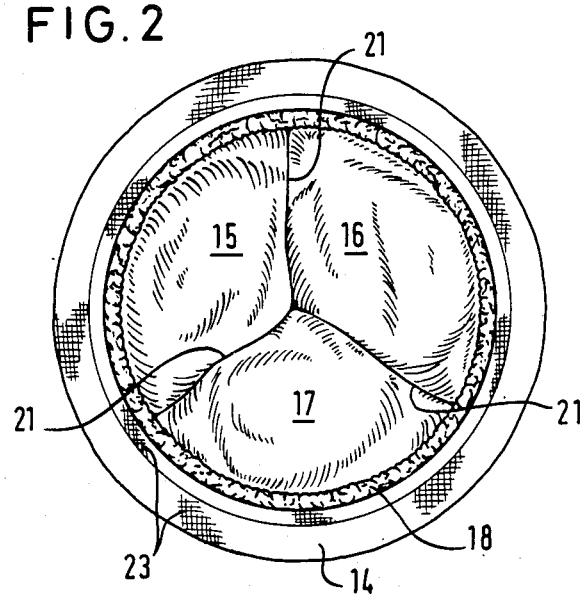
Figure 4:
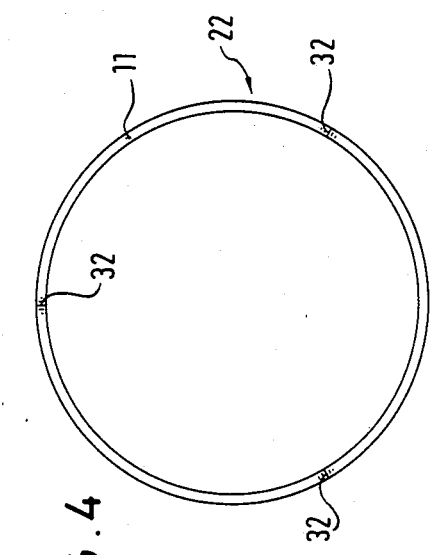
Figure 3:
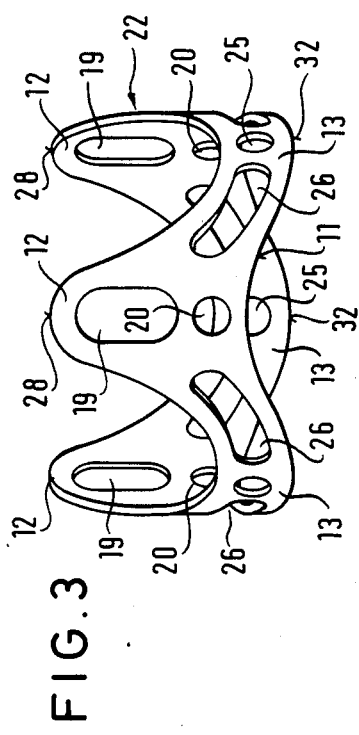

The invention is subsequently described by examples referring to the drawings in which represent:

FIG. 1 a side view of a heart valve prosthesis,

FIG. 2 a view of the object in FIG. 1 as seen from below,

FIG. 3 a side view of the supporting frame used in the artificial heart valve prosthesis depicted in FIGS. 1 and 2, FIG. 3a the supporting frame according to FIG. 3 evolved into a plane and FIG. 4 a view of the supporting frame according to FIG. 3 from below.

According to FIGS. 1 and 2 the supporting frame 22 (FIGS. 3, 4) which is covered on both sides with a polyester or dacron fabric 23 and consists itself of an acetyl resin, Delrin for example, has an essentially circular, cylindrical shape. On the lower end face or lower edge 11 the material 23 has been folded to form a suture ring 14 in which an elastic supporting ring can be placed surrounding the lower edge 11 of the supporting frame 22. The suture ring 14 is determined for suturing the heart valve prosthesis to human tissue, to the aorta for example. According to FIGS. 3, 3a and 4 the supporting frame consists of strip- or band-like material coiled up to a cylindrical shape, the thickness of which is about 1/40th of the external diameter of the carrier frame 22.

Figure 3A:
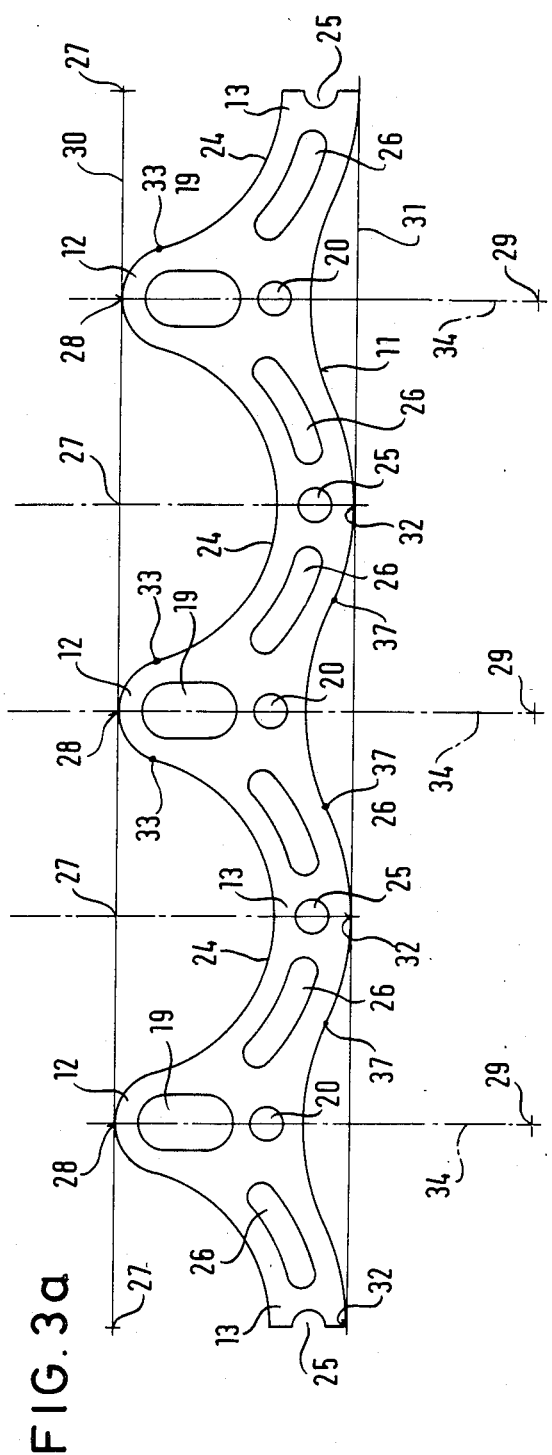

As is especially apparent in FIG. 3 and from the planar evolution shown in FIG. 3a, the band-like material has a gently waved annulus 13 with three complete undulations, each undulation consisting of a wave crest and a wave trough and a post 12 extending axially in the opening direction of the leaflets 15, 16, 17, (FIGS. 1, 2) from each crest.

Each post 12 has an axially directed oblong perforation in the shape of two semicircles mutually connected by straight lines. The radius of the semicircles is 0.64 times the external diameter of the supporting frame 22. The distance of both centres of the semicircles is about 1/10th of the external diameter of the supporting frame 22.

In the region of the apices 28 the posts 12 are rounded in correspondence to the upper semicircle of the oblong perforations 19 so that a width of material equalling 1/16th of the external diameter of the supporting frame 22 remains between the oblong perforations 19 and the upper end face or edge 24 of the posts 12.

Between two adjacent posts 12 the annulus 13 is bordered above by the upper edge 24 having the shape of a concave arc of a circle with the centre of curvature 27 situated in the middle of the connecting line 30 extending between the apices 28 of two adjacent posts 12. In the evolved form of FIG. 3a the upper edge 24 is approximately semi-circular in shape and merges through a reversing point 33 into the upper region of the posts 12 including the apices 28.

At the side of the perforation 19 facing away from the apex 28 a round hole 20 is provided in the annulus 13, the diameter of which is smaller than the external diameter of the supporting frame 22 by a factor of 0.093. The hole 20 is positioned in the middle between the oblong perforation 19 and the lower edge 11 of the annulus 13.

The lower edge 11 of the supporting frame 22 has a concave circular curvature in the region where the posts 12 are positioned. The centre of curvature 29 lies on the mid-axis 34 of the oblong perforation 19 in distinct distance from the connecting line 31 between adjacent apices 32 of the undulating lower edge 11, that is on the side of the connecting line 31 which faces away from the post 12. The preferable distance between the centre of curvature 29 and the connecting line 31 should be about half of the external diameter of the supporting frame 22. The radius of the circle around the centre of curvature 29 is about 50% larger than the radius of the circle around the upper centre of curvature 27, and is conveniently 0.6 times the external diameter of the supporting frame 22. The centres of curvature 27 and 29 are displaced peripherally by an angle of 60°. The apices 28 and 32 are also displaced peripherally by an angle of 60°. The circularly curved portion of the lower edge 11 with the centre of curvature 29 merges through reversing points 37 into circular convex curved portions lying in the region of the apices 32 and having approximately the same radius of curvature as the region with the centre 29.

In the middle of the band-shaped annulus 13 there is a circular boring 25 at each of the peripheral points where the apices 32 are positioned, having a diameter which is smaller than the external diameter of the supporting frame 22 by a factor of 0.064.

A longitudinal slot 26 is positioned to both sides of the boring 25 at a distance of approximately the diameter of the boring 25, the slot 26 being curved in correspondence to the circular concave part of the upper edge 24 and extending parallel to this part of the upper edge 14. The slots 26 extend approximately to the origin of the posts 12 and terminate in a distance from the oblong perforations 19 and the holes 20, respectively which corresponds approximately to the width of the oblong perforations 19. The edge 11 runs parallel to the upper edge 24 in the region of the apices 32.

Due to the shape of the annulus 13 which according to invention undulates only slightly, and due to the posts 12 which according to invention have a relatively short axial length and due to the inventive distribution of perforations, holes, borings, and slots in the supporting frame 22, the supporting frame is, after the attachment of dacron material 23, according to FIGS. 1 and 2, ideally suited for the attachment of a kangaroo aortic valve including the aortic stump 40. Within this carrier frame 22 the leaflets 15,16,17 (FIGS. 1, 2) can open perfectly and completely and also close without impedement. Due to the construction of the carrier frame according to the present invention excellent elasticity is obtained which corresponds to a high degree to the elasticity of the aorta or that section of the heart into which the prosthesis is implanted. Thus the heart valve prosthesis does not affect the natural deformations of those parts of the human tissue it comes into contact with, to a harmful degree.

Furthermore, the numerous perforations in the plastic supporting frame 22 furnish highly satisfactory possibilities for fastening on the dacron fabric to the pulled over.

After completion of the supporting frame 22 as shown in FIG. 3 the dacron fabric is pulled over and sutured in the usual manner. According to FIGS. 1, 2 subsequently the aortic valve of a kangaroo including the aortic stump 40 which have been deadened and preserved by fixation, is inserted into the supporting frame 22 which is covered with the fabric 23. The aortic valve consists of the annulus fibrosus 18 as well as of the three leaflets 15,16,17 originating therefrom, namely the right leaflet 15, the a-coronary leaflet 16, and the left leaflet 17. Sometimes leaflets are called velums.

For mounting the annulus fibrosus 18 is positioned at the lower edge 11 of the supporting frame 22 and the aortic stump 40 extending from the annulus fibrosus 18 and being cut out according to the shape of the edge 24 (FIG. 3a) is arranged in the interior along the annulus 13 and the posts 12 and is sutured in the area of the upper edge 24 (FIGS. 3, 3a) with the fabric 23, whereby the suture 35 is formed. According to FIG. 2 the annulus fibrosus 18 is sutured to the fabric 23 at the suture ring 14, whereby the suture 36 (FIG. 1) is formed.

In the vicinity of the right leaflet small remnant of muscular tissue of the ventricular septum (not shown) adhering to the annulus fibrosus is present. Due to the use of a kangaroo aortic valve the size of this remnant of muscular tissue in the radial dimension is so small and its thickness so insignificant that the freedom of movement of the right leaflet is practically unimpeded when the aortic valve opens.

After implanation to the human body the heart valve prosthesis works according to the invention in the following manner:

When a pressure is developed on the lower or entrance side of the prosthesis where the left ventricle is situated, the leaflets 15,16,17 open upwards in a valve-like manner and lead, due to the design according to invention, to an opening cross-section of at least 70%, generally 75% and under circumstances to even 80% of the cross-section area of the aortic lumen. Thus the pressure gradient arising on both sides of the heart valve prosthesis during opening is kept at a desirable minimum. When the pressure conditions are reversed the valves 15, 16, 17 return to their resting position as can be seen in FIGS. 1, 2, whereby they come into contact with each other and form a seal along the commissure lines 21 in FIG. 2 so that any leaking of blood is prevented.

What we claim is:

1. Heart valve prosthesis with a fixed, integral aortic valve of an adult kangaroo which is positioned in a resiliently flexible, fabric-covered supporting frame having substantially the shape of a cylinder with a substantially circular cross-section and consisting of an axially slightly undulatory annulus comprising three complete waves and of three rounded posts which are positioned at equidistant angles and extend axially from the wave apices and furthermore having a number of perforations, the fabric being shaped as a suture ring near the end face opposite to the posts, the annulus fibrosus, from which the three aortic leaflets originate and in the area of which muscular tissue of the ventricular septum is to be found, extending along the end face of the supporting frame opposite to the posts and being sutured there to the fabric, and the aortic wall or stump, which is cut according to the shape of the supporting frame, being mounted within the annulus and said posts and being sutured to the fabric along the end face of the supporting frame on the side of the posts, in which each of the three leaflets protrude substantially unimpeded from the annulus fibrosus into the aortic lumen, without being coalesced with muscular tissue of the vertricular septum.

2. Heart valve prosthesis according to claim 1 in which the posts of the supporting frame comprise oblong perforations with an axially oriented longitudinal axis which extend into the annulus, the ratio of the length of the oblong perforations to the external diameter of the supporting frame being perferably 0.2 to 0.3.

3. Heart valve prosthesis according to claim 3, in which the shape of the oblong perforations is that of two semicircles connected by straight lines, their radius being 1/14th to 1/17th of the external diameter of the supporting frame.

4. Heart valve prosthesis according to claim 1 in which the annulus has circular holes at the position where the posts are provided, the diameter of the holes being 1/10th to 1/13th of the external diameter of the supporting frame.

5. Heart valve prosthesis according to claim 1 in which the annulus has a central boring in the middle between two posts, the diameter of which is 1/14th to 1/17th of the external diameter of the supporting frame.

6. Heart valve prosthesis according to claim 1 in which the end face of the supporting frame on the side of the posts is shaped in a concave circular manner between the posts, the radius being ½ to ⅓ the external diameter of the supporting frame, and the center of curvature being positioned in the middle of the connecting line between the apices of two neighboring posts.

7. Heart valve prosthesis according to claim 1 in which the middle of the annulus between each post and the midline between two posts has a longitudinal slot following the curvature of the annulus with a width equalling 1/14th to 1/17th of the external diameter of the supporting frame, each slot having a peripheral distance from the middle of the posts of about 1/7th to 1/9th of the external diameter of the supporting frame, and each slot having, if necessary, a peripheral distance from the circular boring of 1/14th to 1/17th of the external diameter of the supporting frame, and the width of the annulus beside the circular boring and the slots, respectively, being 1/14th to 1/17th of the external diameter of the supporting frame.

8. Heart valve prosthesis according to claim 1 in which the annulus beyond the posts has a width 1/6th to ¼th of the external diameter of the supporting frame.

9. Heart valve prosthesis according to claim 1 in which the edge on the side facing away from the posts is shaped in a concave circular manner in the region of the posts, the radius being 0.5 to 0.7 times the external diameter of the supporting frame and the center of curvature conveniently lying in the midaxis of the posts and the distance of each center of curvature from the connecting line between the apices facing away from the posts being 0.4 to 0.5 times the external diameter of the supporting frame.

10. Heart prosthesis according to claim 1 in which the axial length of the supporting frame is 0.58 to 0.62 times its external diameter.

11. Heart valve prosthesis according to claim 1 in which the material thickness of the supporting frame is 1/35th to 1/48th of the external diameter of the supporting frame.

* * * * *